United States Patent [19]

Dadson et al.

[11] Patent Number: 4,983,161
[45] Date of Patent: Jan. 8, 1991

[54] METHOD FOR USING A CONNECTOR CAP AND COVER THEREFOR

[76] Inventors: Joseph E. Dadson, 7 Harrow Smith Place, Richmond Hill, Ontario, Canada, L4E 2E1; Mahesh Agarwal, 7 Grant's Place, Markham, Ontario, Canada, L3S 2W2

[21] Appl. No.: 380,037

[22] Filed: Jul. 14, 1989

[30] Foreign Application Priority Data

Feb. 24, 1989 [CA] Canada .................................. 592017

[51] Int. Cl.⁵ ................................................ A61M 1/00
[52] U.S. Cl. ....................................... 604/28; 604/29; 604/256; 604/905
[58] Field of Search ................... 604/28, 29, 256, 280, 604/283, 411, 905

[56] References Cited

U.S. PATENT DOCUMENTS

| | | | |
|---|---|---|---|
| 4,346,703 | 8/1982 | Denneley et al. | 604/29 |
| 4,431,424 | 2/1984 | Svensson | 604/33 |
| 4,432,764 | 2/1984 | Lopez | 604/283 |
| 4,624,664 | 11/1986 | Peluso et al. | 604/256 |
| 4,642,091 | 2/1987 | Richmond | 604/29 |
| 4,778,447 | 10/1988 | Uelde et al. | 604/29 |
| 4,786,281 | 11/1988 | Valentini et al. | 604/256 |
| 4,786,286 | 11/1988 | Cerny et al. | 604/406 |
| 4,810,241 | 3/1989 | Rogers | 604/28 |

OTHER PUBLICATIONS

8216063, U.K. Patent Application, Chernack, M. P., filed 6/2/82, published 6/29/83.

Primary Examiner—John D. Yasko
Assistant Examiner—Adam J. Cermak
Attorney, Agent, or Firm—Shoemaker and Mattare, Ltd.

[57] ABSTRACT

A cap and cover are provided as a separate, disposable adjunct to the process of peritoneal dialysis, the cap and cover being connectable either together or to the two connectors, respectively, which join the patient's catheter (or transfer set) to cycler tubing. The cap and cover are designed in such away as to define internal chambers that contain liquid disinfectant, whereby they can be applied to the respective connectors (when the latter are separated) in a safe and sterile manner.

2 Claims, 2 Drawing Sheets

METHOD FOR USING A CONNECTOR CAP AND COVER THEREFOR

This invention relates to a connector closure for use in medical applications. Its main use is to cap-off and protect from contamination the two mating ends of connectors used by patients undergoing peritoneal dialysis.

BACKGROUND OF THIS INVENTION

The main objective of peritoneal dialysis is to partially replace the natural kidney function. Peritoneal dialysis (PD) can be used for correcting the following medical disorders:
1. Acute and chronic renal failure
2. Severe water retention
3. Electrolyte disorders and
4. Drug intoxication (acute poisoning)

However, PD is the second dialysis choice to the more efficient Hemodialysis treatment. Hemodialysis is a direct treatment of the blood using an extra-corporeal system with an artificial membrane (kidney), while peritoneal dialysis uses the principles of osmosis and diffusion across the peritoneal membrane to indirectly remove toxic substances from the blood, and thereby correct certain electrolyte and fluid imbalances. The extra-corporeal hemodialysis is used more often when rapid and efficient dialysis is necessary because of excessive hospital patient load and/or severe renal failure or drug intoxication.

Hemodialysis is technically more demanding and more restrictive for the patients than peritoneal dialysis, and those along with other medical reasons have resulted in the steadily increasing use of the simpler peritoneal dialysis (PD).

Although PD was developed long before hemodialysis was introduced, it did not receive attention from most of the clinicians until recently. The current advances in PD have led to an increasing number of patients using peritoneal dialysis. Some of these advances have introduced different PD techniques and others have helped to reduce the peritonitis (infection) rate which is by far the most serious complication associated with PD.

During the last 15 years the advances in PD extended the manual PD from acute therapy only, to chronic therapy. Automated PD was made possible by the introduction of the first proportional PD machines and later by the simpler cycler machines. Because of PD machines, Intermittent Peritoneal Dialysis (IPD) was used for both home and hospital treatments. The Continuous Cyclic Peritoneal Dialysis (CCPD) which is an automated form of Continuous Ambulatory Peritoneal Dialysis (CAPD), has proven that it can reduce the risk of peritonitis. However, since CAPD is a simpler form of home PD, the majority of PD patients are trained on this therapy.

With CAPD the patient manually performs four to six fluid exchanges daily. In between exchanges the patient carries the dialysate in the peritoneal cavity for four or more hours. Of all the PD techniques CAPD has the highest peritonitis rate. Repeated peritonitis may cause scarring of the peritoneal membrane and may reduce membrane permeability. This may lead to a premature termination of PD therapy for the patient. The severity and the frequency of peritonitis have led to a number of technical advances, all intended for use with CAPD, but none of these advances has been shown to significantly reduce the peritonitis rate in any controlled studies. The search continues for a device or technique which will remove this impediment from PD and thereby improve its widespread acceptance.

The recent addition of the "Y" tubing set offers the possibility of peritonitis rate reduction in CAPD. However the complexities and unrefined procedures of the "Y" set have not made its operation friendly to patients. Hence, poor patient compliance, which leads to poor aseptic technique, has masked any great beneficial contribution of the "Y" set to the reduction of the peritonitis rate.

Irrespective of how PD is performed, be it manual PD, IPD, CAPD, CCPD or whatever, there is only one major and critical event that is common to all these procedures: the patient has to be connected to and disconnected from the dialysate source. And that is where the highest risk of infection is understood to originate.

GENERAL DESCRIPTION OF THIS INVENTION

This invention provides a simpler, more cost effective, and safer device and technique for use in covering up (capping-off), protecting and/or disinfecting the two mating ends of connectors used by patients undergoing medical treatment in general and PD in particular. Its main purpose is to reduce medical treatment infection rates, and especially to reduce the PD peritonitis rate associated with the connection and disconnection of tubing sets.

There are a number of PD connector caps currently in active use, which are meant to seal and protect the PD catheter connector after disconnection from the solution tubing set. Many of these caps are not packaged with liquid disinfectant and hence do not disinfect the connectors they are supposed to cap-off. The user has to apply disinfectant to the cap in order to disinfect the PD connector. Applying disinfectant to the cap is time-consuming, messy and often requires the use of expensive prep kits.

Some of these caps, which are meant to disinfect connectors, are supplied with embedded absorbents soaked with disinfectant. Often these absorbents are dry at the time of use. Even when wet, the absorbents do not contain enough disinfectant to provide effective fluid path disinfection of the PD catheter connectors. Also, they are not designed to disinfect the outside of the PD connectors.

Most current connector caps are supplied without protective covers. For the few that have them, the protective covers are not designed to serve any useful function. After they have been removed from the connector caps, they are discarded.

In the present invention, the cover for the PD catheter connector cap is designed to serve a very useful purpose: it is used to cover, protect and disinfect the solution tubing connector (this being the connector that engages the patient's catheter connector during the fill and drain stages of PD). In order to differentiate between the parts of this invention, the main body (the male part i.e., the closure for the PD catheter connector) is referred to as the cap. Its mating cover (the female part) is referred to as the cover.

This invention enables quick connection and disconnection of the PD catheter (or PD transfer set) to and from the solution tubing set respectively, and will be referred to hereinafter as the quick connect cap or QC Cap.

The quick connect cap of the present invention is generally cylindrical in shape and comes in two parts. The inner part of each is hollow and capable of carrying a disinfecting agent such as Betadine, providone-iodine or amuchina. The cover is normally screwed on top of the cap. The two halves are presented here with mating threads. However, the two can be of any compatible shapes and fittings. In this invention the cover is a female and the cap is a male. However the reverse is possible depending on the type of mating of the medical connectors in use for the particular therapy.

At a termination or an interruption of PD treatment, the PD connector is disconnected from the solution tubing set. This invention provides a cap to close and protect the connector attached to the patient's catheter. The cover of the cap is used to cover and protect the connector attached to the solution tubing set. Thus, during the disconnected interval, the two mating connectors are fully protected and continuously disinfected.

The invention makes reconnection very simple and quick. As soon as the protective covers on the two mating connectors are removed (i.e., the two parts of this invention—the cap and the cover), the mating connectors are reconnected right away without any reconditioning. No prep kits are required. No connector disinfection is needed, therefore operational cost is reduced.

To start a new treatment, the protective closure (the cap of this invention) covering the patient's connector is removed, whereupon the connector is immediately inserted into the connector of the new solution tubing set. There is no need to disinfect the patient's connector before connecting it to the solution tubing set, and the connector of the new tubing set is supplied in sterile condition. No prep kit is required. Hence, initiating PD treatment is easier and quicker. Also operational cost is greatly reduced. For the non-clinicians and the inexperienced patients this invention eliminates the tedious and critical aseptic PD on-procedures which when violated often cause peritonitis.

The additional benefits of this invention may go mainly to patients. Patients on in-hospital IPD are attached to the machines for a 12 to 24 hour treatment period. For these patients there is no privacy and they are nurse-dependent with respect to attending washroom facilities. In fact, all of their activities are confined to bed. Often they become very fatigued at the end of dialysis because of their immobility during the long hours of treatment. With this invention, patients on IPD can safely disconnect completely from the machine to go for laboratory test, have their meals, walk about and use washroom facilities with great ease, confidence and safety.

This invention provides, for the PD operation, a quick, safe, easy consistent and inexpensive means of initiating, interrupting and terminating patient treatments.

More particularly, this invention provides, in combination:

a connector which defines a portion having an external thread and a cylindrical internal bore, and a cap closing the internal bore, the cap comprising an integral body having:

(a) a substantially cylindrical central probe snugly contained within the said internal bore of the connector, thus sealing the same, the probe having a leading end and a central axis, (b) a first chamber within the probe, the first chamber opening only through said leading end and containing liquid disinfectant, (c) a cylindrical portion substantially coaxial with the probe and having an internal thread threadably engaging said external thread on said portion of the connector, (d) and a second chamber of annular configuration lying outside of the probe and inside of the cylindrical portion, said second chamber containing liquid disinfectant.

More particularly, this invention provides, in the process of peritoneal dialysis wherein a patient catheter is connected to dialysate tubing by a first connector communicating with the catheter and a second connector communicating with the dialysate tubing, one of said connectors defining a sleeve with an external thread and a cylindrical inner bore through which dialysate can flow, the other of said connectors defining an internal thread adapted to engage said external thread and a cylindrical central probe adapted to snugly enter said inner bore when the threads are in engagement, the probe having an internal passage through which dialysate can flow, a method of aseptically disconnecting said connectors to free the patient temporarily from the dialysis apparatus, comprising the steps:

(a) providing a cap and a cover therefore, one of said cap and cover defining a cylindrical portion having an internal thread capable of engaging said external thread, the other of said cap and cover defining an external thread capable of engaging said first-mentioned internal thread, said other of said cap and cover defining a blind, internal cylindrical bore coaxial with the axis of said last-mentioned external thread, said last-mentioned bore containing liquid disinfectant, said one of said cap and cover defining a cylindrical central probe coaxial with said internal thread and having a diameter such that the probe can snugly enter the said internal cylindrical bore of said other of the cap and cover whenever said last-mentioned internal thread is in engagement with said last-mentioned external thread, the probe having a leading end, a first chamber within the probe containing liquid disinfectant, the chamber opening only through the leading end of the probe, and a second chamber of annular configuration lying outside of the probe and inside of the cylindrical portion of said one of said cap and cover, the second chamber containing liquid disinfectant, (b) in any order, disconnecting said connectors from each other, and disconnecting said cap from said cover, (c) in any order, connecting said one of said connectors to said one of said cap and cover, and connecting said other of said connectors to said other of said cap and cover.

GENERAL DESCRIPTION OF THE DRAWINGS

One embodiment of this invention is illustrated in the accompanying drawings, in which like numerals denote like parts throughout the several views, and in which.

DETAILED DESCRIPTION OF THE DRAWINGS

Figure 3:
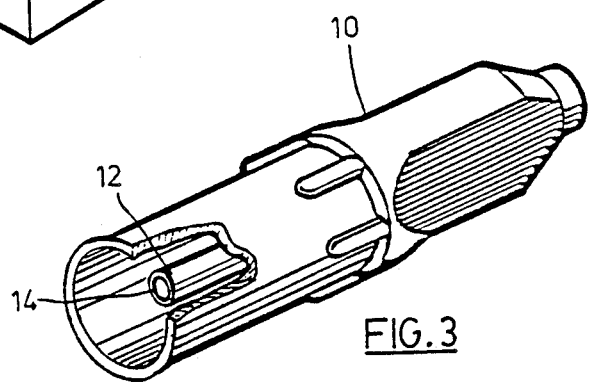
FIG. 3 is a perspective view of the QC cap of this invention, with a portion broken away to show the internal probe.

Attention is first directed to FIG. 3, which shows an integral QC cap at 10 which includes a substantially cylindrical central probe 12, with a leading end 14. The probe 12 is hollow, as can be seen at 16 in FIG. 5, the hollow interior of the probe 12 communicating with a recessed chamber 18. It will be seen that the chamber 18, including the hollow interior 16 of the probe 12, is blind at the rightward end in FIG. 5, and opens only through the leading end 14 of the probe 12.

The cap 10 further includes a cylindrical portion 20 which is substantially coaxial with the probe, and has an internal thread 22, the purpose of which will become clear in what follows.

The cap 10 further defines an additional chamber 24 of annular configuration lying outside of the probe 12 and inside of the cylindrical portion 20.

Figure 4:
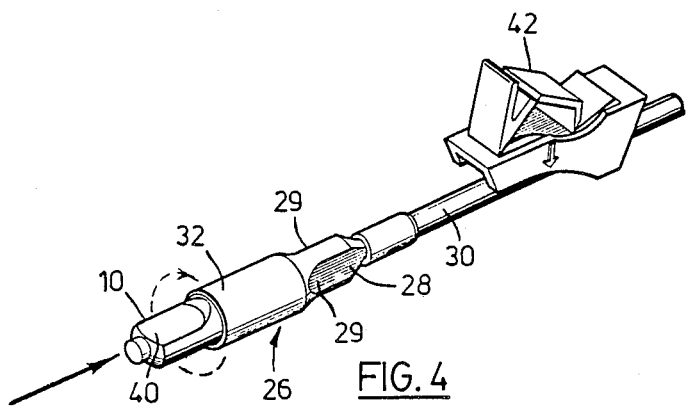
FIG. 4 is a perspective view showing a QC cap covering and protecting the connector for the patient catheter or patient transfer set.
Figure 5:
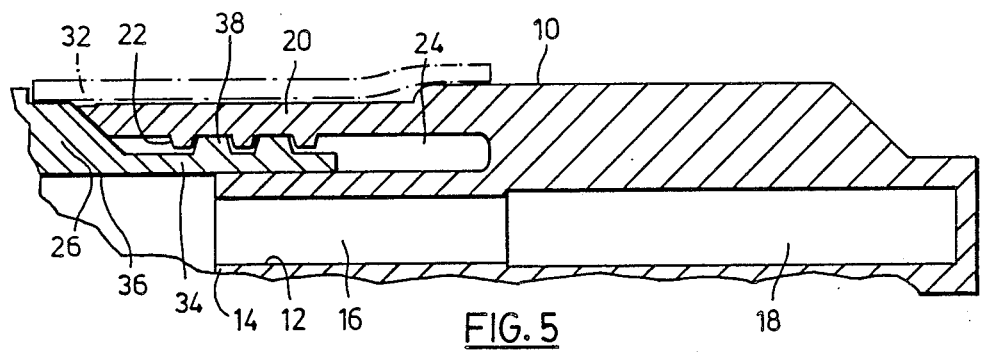
FIG. 5 is a partial axial sectional view, to a larger scale, of a QC cap mated with a catheter connector or a transfer set connector.

The cap which is illustrated at 10 in FIG. 5 is adapted to close a connector shown at 26 in FIG. 4, and shown partly in section in FIG. 5.

Looking at FIG. 4, the connector 26 has a rearward portion 28 exhibiting two flats 29 for ease of handling, and having a standard tubular portion adapted to connect to a flexible tubing 30 which may be either the patient's catheter or the tube of a transfer set in turn connected to the patient's catheter. In FIG. 4, the leftward end of the connector 26 is covered by a resilient sleeve member 32 which is shown in broken lines in FIG. 5. The sleeve member 32 covers and protects a neck portion 34 (see FIG. 5) having an open central passageway 36, and having an external thread 38. As can be seen in FIG. 5, the external thread 38 engages the internal thread 32, and at the same time the leading end 14 of the probe 12 enters the passageway 36. The probe 12 is sized to be snugly received in the passageway 36 (referred to in the claims as a cylindrical internal bore).

The figures show that the remainder of the cap 10 (the portion to the right in FIG. 5) is shaped to define two flats 40, on opposite sides, to facilitate manipulation.

In FIG. 4, a conventional clamp is shown at 42.

FIG. 4 can also be taken to represent the condition of a typical transfer set, as packaged. In accordance with one aspect of this invention, the packaged transfer set (ready to be connected to the patient's catheter and then to the tubing set) would include a cap 10 exactly as described above. When the connector 26 (FIG. 4) is ready to be connected to the tubing set, the cap 10 shown in FIG. 4 (i.e., the original cap closing the connector 26 of a transfer set in the packaged condition) is removed by rotating counterclockwise and then discarded.

The connector 26 shown in FIG. 4 is then ready to be connected to the cycler tubing leading to one or more dialysate bags and one or more drain bags or the equivalent.

Figure 6:
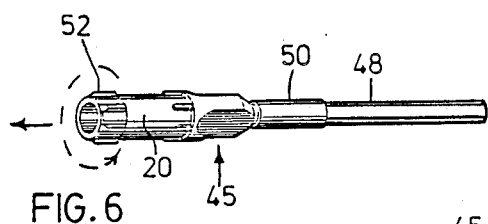
FIG. 6 shows a connector as supplied with cycler tubing, along with a typical removable cover.

FIG. 6 shows the "patient end" of the cycler tubing, in the condition in which the tubing is packaged. For the most part, the connector shown at 45 in FIG. 6 has the same structure as the cap 10 shown in FIG. 5, with the exception that the internal chamber 18 (FIG. 5) is not closed at the right. Instead, it communicates with an integral, hollow sleeve or pipe portion which is connected to the tubing 48 at the location 50. Since the remaining portions are identical in structure to the cap 10, the same reference numerals are used in FIG. 6. In its packaged condition, the connector 45 is closed by a special disposable cover 52 which is like a closed cap having the same cylindrical portion 34 and external thread 38 as are shown in FIG. 5.

Figure 7:
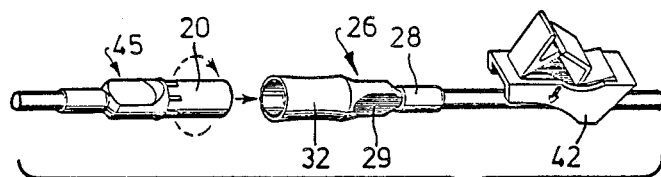
FIG. 7 shows the manner of connection between the patient transfer set connector and the cycler tubing connector of FIG. 6, including the rotary motion for connection.

In FIG. 7, the cycler tubing connector 45 is shown in a position ready to be connected to the connector 26 on the transfer set (i.e., the same connector 26 as is shown in FIG. 4). Connection is made by manually rotating the connector 45 in a clockwise direction, while pushing the cylindrical portion 20 thereof into the resilient sleeve member 32. Preferably, the sleeve member 32 is glued or otherwise securely adhered to the connector 26.

Because both connectors are in sterile condition at the time of being removed from the packaging, it is not essential to coat the mating surfaces with disinfectant, although this can be done if desired.

Once the connectors 26 and 45 have been connected together as described above, the peritoneal dialysis treatment may begin.

Figure 1:
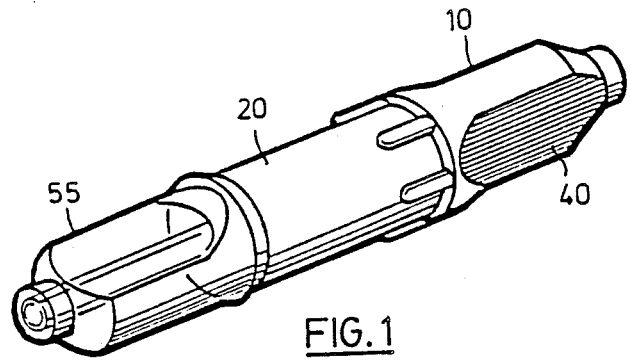
FIG. 1 is a perspective view of a QC cap constructed in accordance with this invention, with a cover in the closed position.

Aside from certain details of construction, the foregoing description may be taken to refer to a conventional "start-up" procedure for peritoneal dialysis using CAPD. In the past, however, once the connectors have been mated together as seen in FIGS. 6 and 7, the patient was required to remain thus connected for many hours at a time, due to the risk of infection in the event of a disconnection between the connectors 26 and 45. In accordance with the present invention, a simple and safe procedure is available to disconnect the patient from the cycler tubing in such a way that he can be reconnected readily and safely. In order to accomplish this, the present invention provides a QC cap and cover as seen in FIG. 1.

Figure 2:
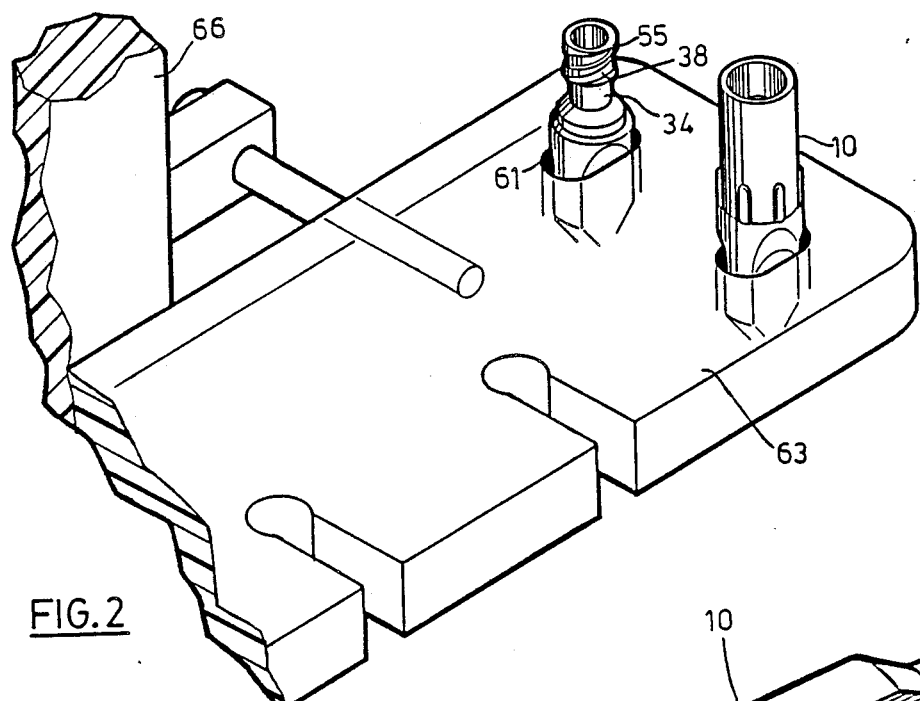
FIG. 2 is a perspective view of the separated cap and cover, located in a temporary holding device.

Looking at FIG. 1, the QC cap 10 is identical to the cap already described with reference to FIG. 5. However, FIG. 1 also shows a cover 55 for the cap 10, the cover being hollow and bottle-like, as can readily be seen by comparing FIGS. 1 and 2. By further comparing with FIG. 5, it can be seen that the cover 55 has the same structure as the connector 26, with the exception of the sleeve 32, and with the exception that the cover 55 does not have an open-ended bore throughout. Instead, the cover 55 defines a closed chamber constituted by the passageway 36 (FIG. 5). However, the cover 55 does provide a cylindrical portion 34 with external threads 38, just as seen in FIG. 5. These portions are not visible in FIG. 1.

In the packaged condition, the cap 10 and cover 55 combination is provided with liquid disinfectant within the central passageway 36 of the cover, within the chamber 18 (and 16), and within the annular chamber 24.

Figure 8:
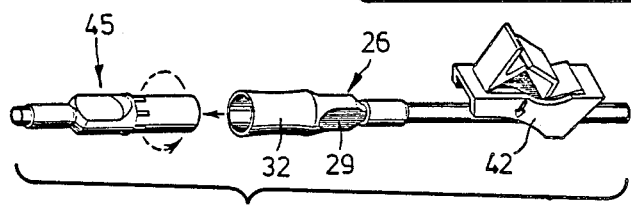
FIG. 8 is similar to FIG. 7, but shows the rotary motion for disconnection.
Figure 9:
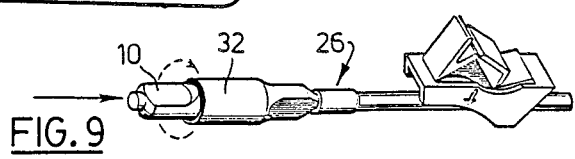
FIG. 9 shows the connection of the QC cap to the connector of the patient transfer set.

In order to disconnect the patient from the PD apparatus, the following steps are taken. First the tubing 48 connected to the connector 45 is clamped. Then, the patient's transfer set is clamped using the clamp shown at 42 in FIGS. 7 and 8. The operator should then mask and hand wash, following which the QC cap (complete with cover) can be taken out of its package and placed on a clean surface.

Next, the cycler set is disconnected from the transfer set by holding the connector 26 stationary and rotating the connector 45 in the counterclockwise direction. It is important to keep the connector 26 stationary, in order not to twist the transfer set.

The cover 55 is then removed from the cap 10, and these portions may be placed in appropriate openings 61 in a plate 63 supported from a standard 66 or other appropriate portion of the apparatus.

The cap 10 is then connected to the connector 26 of the transfer set by pushing it into the sleeve 32 while rotating in the clockwise direction. Next, the connector 45 of the cycler set is capped off with the cover 55.

At this point, both of the previously connected connectors are closed in a safe, antiseptic manner, allowing the patient to leave.

If the disconnection was required due to an unforeseen interruption in the PD procedure, for example the use of a washroom, then the patient can later return to the apparatus, remove the cap 10 and the cover 55 from their respective connectors, and reattach the freed connectors. Because of the liquid antiseptic in the various chambers of the cap 10 and cover 55, the risk of infection from reconnecting the connectors will be virtually eliminated. It is important to note, however, that the same cap 10 and cover 55 should not be re-used at a later point for the same purpose. They should be discarded after each single use, and a new cap/cover combination should be utilized for a later interruption.

In the event that the disconnection of the connectors 26 and 45 occurs simply at the end of a treatment, the procedure would be to discard the cycler set tubing, and retain the cap 10 on the connector 26 of the transfer set until the next dialysis treatment.

While one embodiment of this invention has been illustrated in the accompanying drawings and disclosed hereinabove, it will be evident to those skilled in the art that changes and modifications may be made therein without departing from the essence of this invention, as set forth in the appended claims.

The embodiments of the invention in which an exclusive property or privilege is claimed are defined as follows:

1. In the process of peritoneal dialysis wherein a patient catheter is connected to dialysate tubing by a first connector communicating with the catheter and a second connector communicating with the dialysate tubing, one of said connectors defining a sleeve with an external thread and a cylindrical inner bore through which dialysate can flow, the other of said connectors defining an internal thread adapted to engage said external thread and a cylindrical central probe adapted to snugly enter said inner bore when the threads are in engagement, the probe having an internal passage through which dialysate can flow, a method of aseptically disconnecting said connectors to free the patient temporarily from the dialysis apparatus, comprising the steps:

(a) providing a cap and a cover therefore, one of said cap and cover defining a cylindrical portion having an internal thread capable of engaging said external thread, the other of said cap and cover defining an external thread capable of engaging said first-mentioned internal thread, said other of said cap and cover defining a blind, internal cylindrical bore coaxial with the axis of said last-mentioned external thread, said last-mentioned bore containing liquid disinfectant, said one of said cap and cover defining a cylindrical central probe coaxial with said internal thread and having a diameter such that the probe can snugly enter the said internal cylindrical bore of said other of the cap and cover whenever said last-mentioned internal thread is in engagement with said last-mentioned external thread, the probe having a leading end, a first chamber within the probe containing liquid disinfectant, the chamber opening only through the leading end of the probe, and a second chamber of annular configuration lying outside of the probe and inside of the cylindrical portion of said one of said cap and cover, the second chamber containing liquid disinfectant, (b) in any order, disconnecting said connectors from each other, and disconnecting said cap from said cover, (c) in any order, connecting said one of said connectors to said one of said cap and cover, and connecting said other of said connectors to said other of said cap and cover.

2. The method claimed in claim 1, in which the recited steps are followed by the steps:

(d) in any order, disconnecting said one of said connectors from said one of said cap and cover, and disconnecting said other of said connectors from said other of said cap and cover, and (e) reconnecting said connectors to each other.

* * * * *